US006567162B2

(12) United States Patent
Koren et al.

(10) Patent No.: US 6,567,162 B2
(45) Date of Patent: May 20, 2003

(54) RECONFIGURABLE APPARATUS AND METHOD FOR INSPECTION DURING A MANUFACTURING PROCESS

(75) Inventors: Yoram Koren, Ann Arbor, MI (US); Reuven Katz, Haifa (IL)

(73) Assignee: The Regents of the University of Michigan, Ann Arbor, MI (US)

( * ) Notice: Subject to any disclaimer, the term of this patent is extended or adjusted under 35 U.S.C. 154(b) by 98 days.

(21) Appl. No.: 09/871,065

(22) Filed: May 31, 2001

(65) Prior Publication Data

US 2002/0180960 A1 Dec. 5, 2002

(51) Int. Cl.[7] .............................................. G01N 21/00
(52) U.S. Cl. ................................................... 356/237.2
(58) Field of Search .............................. 356/237.2, 600, 356/601, 614, 625; 73/865.8, 865.9, 866; 250/206.1, 208.1, 208.2; 29/33 P; 414/800

(56) References Cited

U.S. PATENT DOCUMENTS

| | | | |
|---|---|---|---|
| 4,663,625 A | | 5/1987 | Yewen |
| 4,899,218 A | | 2/1990 | Waldecker et al. |
| 4,901,218 A | * | 2/1990 | Cornwell ........................ 700/2 |
| 4,963,017 A | | 10/1990 | Schneiter et al. |
| 5,095,204 A | * | 3/1992 | Novini .................... 250/223 B |
| 5,114,230 A | * | 5/1992 | Pryor .......................... 356/625 |
| 5,374,988 A | | 12/1994 | Wertz et al. |
| 5,402,582 A | | 4/1995 | Raab |
| 5,431,599 A | * | 7/1995 | Genco ......................... 454/187 |
| 5,510,603 A | * | 4/1996 | Hess et al. ................... 235/454 |
| 5,510,625 A | | 4/1996 | Pryor et al. |
| 5,803,419 A | | 9/1998 | Nicot |
| 5,825,017 A | | 10/1998 | Pryor |
| 5,871,391 A | | 2/1999 | Pryor |
| 5,910,894 A | | 6/1999 | Pryor |
| 5,914,876 A | * | 6/1999 | Hirai ........................... 700/87 |
| 5,917,726 A | | 6/1999 | Pryor |
| 5,943,750 A | | 8/1999 | Koren et al. |
| 5,969,339 A | * | 10/1999 | McMurray et al. ..... 250/223 R |
| 5,984,499 A | * | 11/1999 | Nourse et al. .................. 700/5 |
| 6,094,793 A | | 8/2000 | Szuba |
| 6,134,013 A | | 10/2000 | Sirat et al. |
| 6,134,507 A | | 10/2000 | Markey, Jr. et al. |
| 6,166,811 A | | 12/2000 | Long et al. |
| 6,172,748 B1 | | 1/2001 | Sones et al. |
| 6,349,237 B1 | * | 2/2002 | Koren et al. ................... 700/96 |
| 6,383,057 B1 | * | 5/2002 | Bartlett et al. .................. 451/7 |
| 6,415,191 B1 | * | 7/2002 | Pryor .......................... 700/95 |

OTHER PUBLICATIONS

International Search Report for International Application No. PCT/US02/19212, mailed Oct. 3, 2002.
"The Development of Part Measurement System", Dr. J. Yuan, Presented at Ford Motor Company, Sep. 20, 2000.

* cited by examiner

Primary Examiner—Zandra U. Smith
Assistant Examiner—Gordon J Stock, Jr.
(74) Attorney, Agent, or Firm—Kirkpatrick & Lockhart LLP

(57) ABSTRACT

An inspection apparatus, system and method for inspecting parts during a manufacturing process. The apparatus comprises a conveyor line for moving a part during a manufacturing process and a plurality of sensors and cameras mounted on stationary supports around the conveyor line. The conveyor line may be a part of or adjacent to the production line. The sensors measure a characteristic of a first part and produce an inspection output, and can be reconfigured for inspection of at least one different characteristic of a second part or for re-inspection of the first part at a different stage of the manufacturing process. The apparatus may include a computer system that receives the sensor inspection outputs and produces operator-accessible information. The apparatus may include means for identification of the parts. Alternatively, the parts may be stationary and the supports on which the sensors are mounted may be moving relative to the parts.

23 Claims, 6 Drawing Sheets

RECONFIGURABLE APPARATUS AND METHOD FOR INSPECTION DURING A MANUFACTURING PROCESS

FEDERALLY SPONSORED RESEARCH

Certain of the research leading to the present invention was sponsored by the United States Government under National Science Foundation (NSF) Grant No. EEC 9529125. The United States Government has certain rights in this invention.

BACKGROUND OF THE INVENTION

1. Field of the Invention

The invention relates to a reconfigurable apparatus and method and, more particularly, to a reconfigurable apparatus and method for inspection of parts during a manufacturing process.

2. Description of the Invention Background

Manufacturers of mass-produced parts and products, such as vehicles, rely on automated inspection machines for quality control and rejection of defective parts. Consumer demand as well as considerations of safety and efficiency have led to the development of inspection systems that rely on machine vision coordinated with robotics and computer aided design to achieve precision and quality.

One such inspection system is the coordinate measurement machine or CMM disclosed in U.S. Pat. No. 5,402,582. The CMM uses three linear scales to measure the coordinates of an object in three-dimensional space. The measurements are made by a multi-jointed mechanical measuring arm, which includes measurement transducers. The CMM is connected to a controller in communication with a computer system that provides output for an operator. CMMs are used to measure a variety of different parts mainly in a metrology lab.

Because of the relatively high costs of CMMs, less accurate and less expensive conventional industrial robots equipped with contact sensors are often used for inspection of parts. Another, more accurate, robot-based system equipped with a non-contact sensor is disclosed in U.S. Pat. No. 6,166,811. This patent discloses a vision system adapted to retrieve data from the non-contact sensor and position data from a position reporting device and synchronize the image data from the sensor with the position data.

CMMs and robot-based systems operate by moving the sensor around the part to take measurements while the part is stationary. The inspection process is done off-line, preferably in an inspection room. It may take several hours to complete the inspection of a complicated automobile engine part. During this inspection time, bad or defective parts may be produced on the assembly line.

There remains, therefore, a need for an improved inspection system that can be used to inspect a family of parts during the manufacturing process, either on or adjacent to the production line and that overcomes the limitations, shortcomings and disadvantages of other known inspection systems.

SUMMARY OF THE INVENTION

The present invention meets the identified needs, as well as other needs, as will be more fully understood following a review of this specification and drawings.

One embodiment of the invention includes an inspection apparatus that comprises a conveyor line for moving a first part during a manufacturing process. The conveyor line is either a part of or adjacent to the moving production line. The inspection apparatus also includes a plurality of non-contact sensors, which are mounted on stationary supports around the conveyor line. One or more of the plurality of sensors may be enclosed within an environmentally-controlled chamber. The sensors measure a characteristic of the first part, such as, for example, parallelism, flatness, profile, etc., and produce inspection outputs. The sensors can be reconfigured for inspection of at least one different characteristic of a second part. The second part may be, for example, a new or redesigned part of the same or a related family. The same part in different orientation with respect to the inspection machine or at a different location along the production line and at a different stage during the manufacturing process may also be re-inspected. The apparatus may include shock absorption or vibration isolators. The apparatus may also include a computer system that receives the sensor inspection outputs and produces operator-accessible information. The apparatus may further include an entrance tag reader and an exit tag reader to read and write information from a tag attached to a fixture that holds the inspected part.

An additional embodiment of the invention also includes a system for inspecting a first part and a second part. The system comprises a conveyor line, a plurality of stationary supports in proximity to the conveyor line and a plurality of non-contact sensors, which are mounted on stationary supports around the conveyor line. The sensors can be reconfigured for inspection of at least one different characteristic of the second part. The same part in a different orientation with respect to the inspection machine or at a different location along the production line and at a different stage during the manufacturing process may also be re-inspected. The apparatus may also include a computer system that has a communication module in communication with the sensors and the conveyor line, and a decision module that compares the inspection outputs for each inspected part with a computer-stored design of the part within predetermined tolerances. The computer system further includes a control module that issues a command when a tolerance is exceeded. The computer system may further include a feedback module in communication with a Numerical Controller (NC) for the manufacture of the inspected part. The command may optionally be sent to a conveyor controller to stop the conveyor line. A command may also optionally be sent to the numerical controller to stop the numerical controller or to modify a predetermined path of the numerical controller.

Another embodiment of the invention, and more particularly of the inspection system, includes a conveyor line, a plurality of stationary supports near the conveyor line and a machine vision system comprising a plurality of non-contact sensors, at least one camera and a machine vision processor that communicates with the sensors and the camera and issues a command to a Programmable Logic Controller (PLC) regarding the production of a first part. The sensors and the camera are reconfigurably mounted on any of the supports such that the inspection system can be quickly reconfigured for inspecting a second part, such as a new or redesigned part of the same or related family of parts or to re-inspect the same part at a different stage of the manufacturing process.

In an alternate embodiment, the inspected part may be stationary and the supports on which the sensors are reconfigurably mounted may be moving in relation to the stationary part.

Another embodiment of the invention includes a method for inspecting parts during a manufacturing process. The method comprises mounting a plurality of non-contact electro-optical sensors in proximity to a moving line holding a first part, measuring at least one characteristic of the first part, producing an inspection output and converting the inspection output to operator-accessible information. The method also includes reconfiguring the sensors for inspection of a second part with different characteristics. The method may further include mounting a camera that interfaces with the sensors and is directed to the conveyor line, and reconfiguring the camera for inspecting the second part.

Yet another embodiment of the invention includes a method for inspecting and re-inspecting a part during a manufacturing process. The method comprises mounting a plurality of non-contact electro-optical sensors in proximity to a moving line holding the part, measuring at least one characteristic of the part at a first stage of the manufacturing process, producing an inspection output and converting the inspection output to operator-accessible information. The method also includes reconfiguring the sensors for inspection of the part at a second stage of the manufacturing process.

It is a feature of at least one embodiment of the invention to provide an inspection system that can be used to inspect a part as the part moves on a production line or adjacent to a production line.

Another feature of at least one embodiment of the invention is to provide an inspection system that is easily and quickly reconfigurable for inspection of a different, new or redesigned, part of the same or related family of parts, and for re-inspection of the same part at different stages of the manufacturing process, including at a different location with respect to the production line or at different orientation with respect to the inspection machine.

It is a feature of yet another embodiment of the invention to provide fast feedback for the correction or modification of the manufacturing process so that the production of defective or nonconforming parts is minimized.

It is another feature of various embodiments of the invention to provide an inspection applicable to a medium or high-volume production of a family of parts where switchovers among the parts within the family may be the practice.

Accordingly, various embodiments of the invention provide solutions to the limitations, shortcomings and disadvantages of other inspection systems and methods. Those of ordinary skill in the art will readily appreciate, however, that these and other details, features and advantages will become further apparent as the following detailed description proceeds.

BRIEF DESCRIPTION OF THE DRAWINGS

In the accompanying drawings, there are shown embodiments of the invention wherein like reference numerals may be employed to designate like parts, if applicable, and wherein.

DETAILED DESCRIPTION OF THE INVENTION

Figure 1:
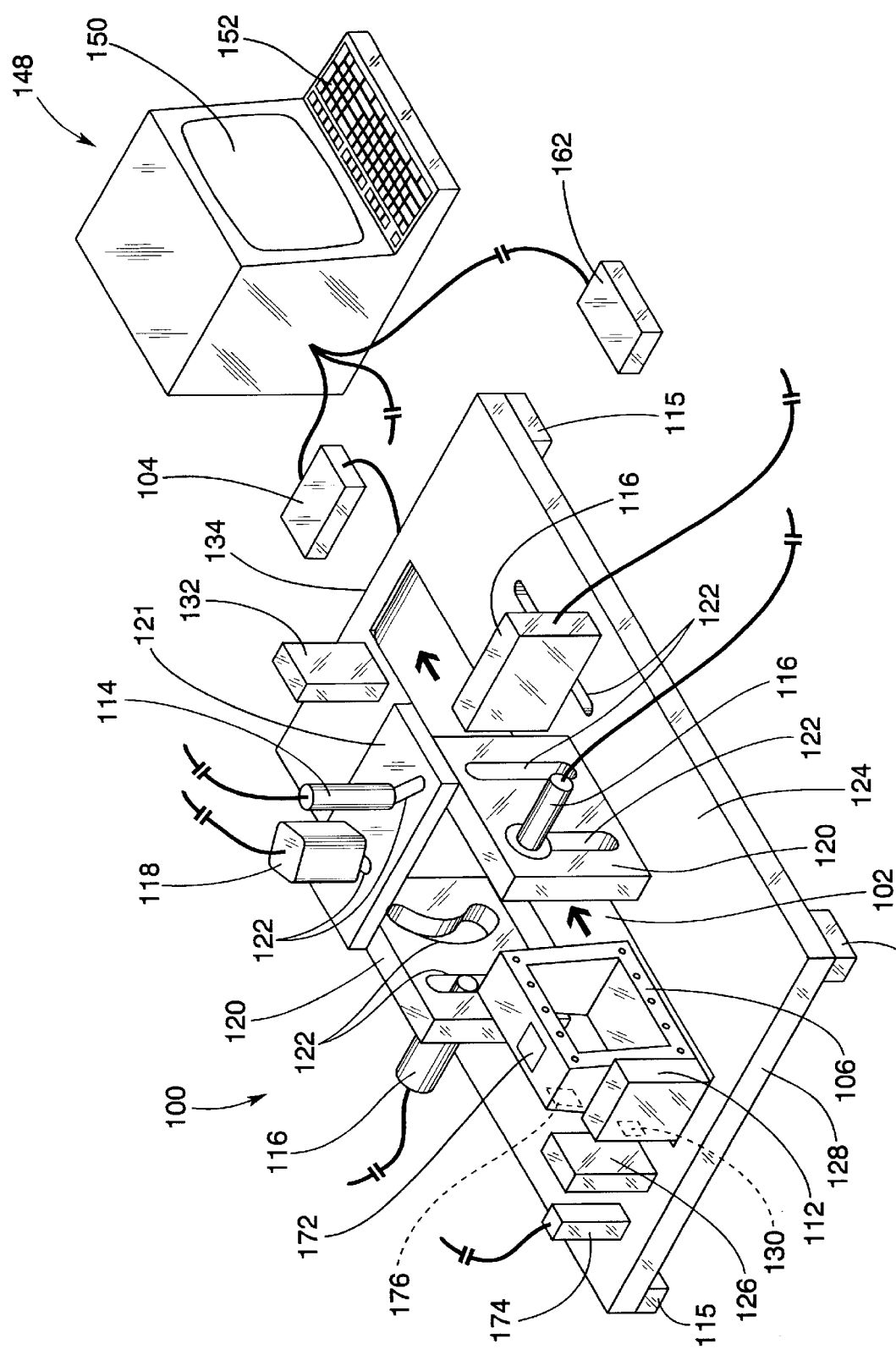
FIG. 1 is a schematic isometric view showing an embodiment of an inspection apparatus according to the invention.

Referring now to the drawings for the purpose of illustrating the invention and not for the purpose of limiting the same, there is shown various embodiments of an apparatus and system for inspecting a first part and a second part that belong to the same or related family of parts, or for re-inspecting the same part at different stages of the manufacturing process. Although the invention is not so limited, the inspection apparatus and system may be used, for example, in the production line of an automotive assembly plant or an automotive machining plant, and each inspection apparatus employed may be dedicated to a single family of parts. An automotive production plant may incorporate, for example, one inspection apparatus for cylinder heads, another one for brakes, and so on. It is to be understood that when reference is made herein to a first part and a second part, the first part is the part that is under inspection at current conditions, and the second part is the part that may be inspected after reconfiguring the apparatus or system. Additionally, more than one inspection apparatus may be placed on or along the production line to inspect the same or different parts at different stages of the manufacturing process. Therefore, the second part may be the original part re-inspected by the same inspection apparatus at a different stage of the manufacturing process or by another inspection apparatus at a different location along the production line. Reference to a part without any qualification, is to be understood as reference to a part under inspection. Furthermore, inspection of a part is understood to include inspection of one or more parts.

FIG. 1 shows an inspection apparatus 100 that includes a conveyor line 102 for moving a part during a manufacturing process. The conveyor line 102 is a moving line or slide that transfers parts during machining/production and may include a belt, or other type of conveyor. The conveyor line may be a part of the production line or may be located adjacent to the production line during the manufacturing process. The conveyor line 102 may be automated and controlled by conveyor controller 104. The conveyor line 102 is, preferably, an accurate linear motion slide.

Figure 2A:
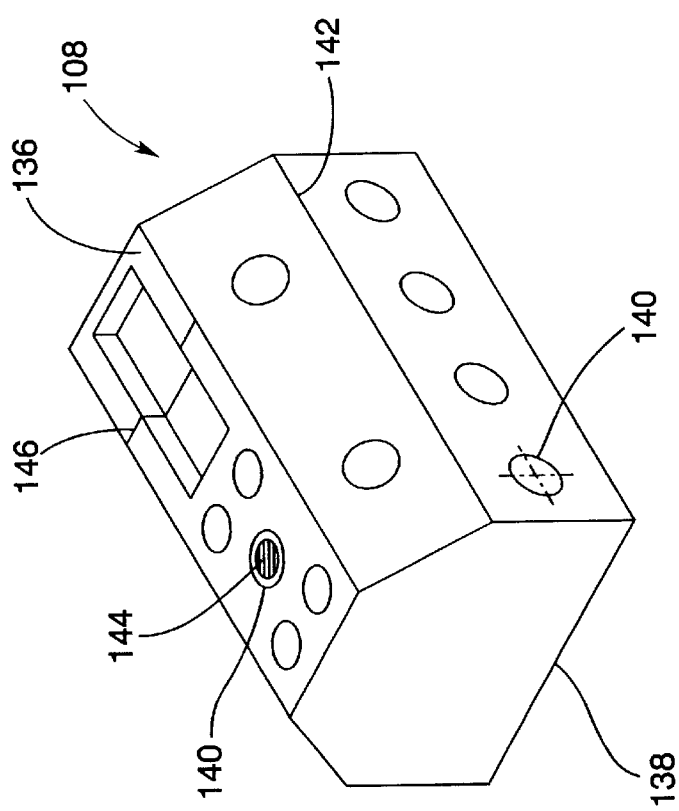
FIG. 2(a) is a schematic isometric view of a first exemplary part that may be inspected by the apparatus of FIG. 1.
Figure 2B:
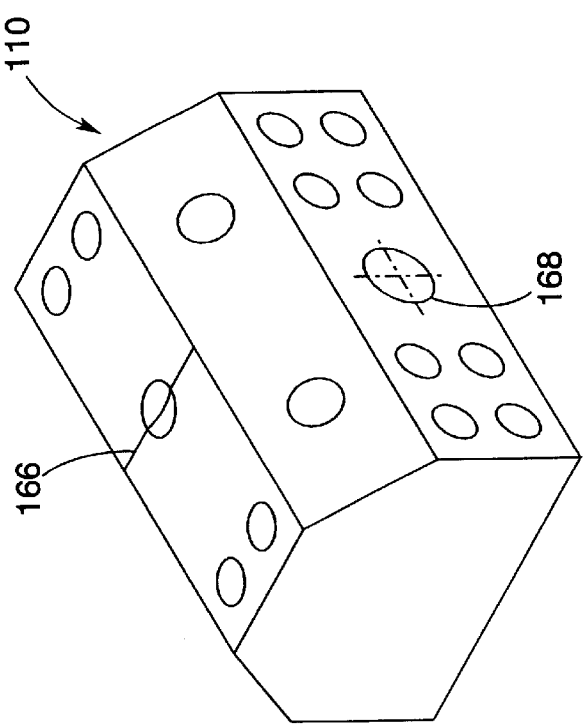
FIG. 2(b) is a schematic isometric view of a second exemplary part that may be inspected by the apparatus of FIG. 1.

A part 106 placed on the conveyor line 102 moves along the apparatus 100. The part 106 may, for example, belong to a family of parts such as cylinder heads. Examples of a first part 108 and a second part 110 are shown in FIGS. 2(a) and 2(b) respectively. The part 106 may be releasably held on a fixture 112 by any type of fasteners that can quickly and accurately hold and release the part, such as precision clamps and grips, which are commercially available.

A plurality of electro-optical devices 114, or detectors for short, are placed around the conveyor line 102. The detectors 114 may include, for example, non-contact sensors 116, including laser-based profilometers, and video cameras and line scanning cameras 118, all of which are commercially available. An example of a fast and accurate non-contact sensor/profilometer that may be used with the invention is the Conoscan 3000, which is manufactured by Optimet Metrolology Limited, Jerusalem, Israel.

The detectors 114, i.e. the sensors 116 and cameras 118, are mounted on one or more stationary supports 120, or moving supports 121 that can also be kept stationary if it is so desired. The supports may be placed, for example, on each side of or above the conveyor line 102. A substrate 124 for the inspection apparatus 100 may also be one of the supports. Each detector 114 may be mounted on a groove 122, which may be straight, arcuate or have other shapes, sizes and configuration, on a respective support 120, so that the detector 114 can be moved or slid along a path defined by the groove 122, or relocated to another groove 122, such that the result is a reconfigured array of detectors 114. The shape, size and length of grooves 122 are, preferably, chosen for a particular family of parts, so that changes from a first part 108, which may represent, for example, the old design for the part, to a second part 110, which may represent the new or redesigned part, can be inspected with accuracy and speed by a single inspection apparatus 100 which is dedicated to the specified family of parts. Because parts within the same family are typically redesigned so that they maintain certain overall dimensional limitations dictated by the character of the family and, therefore, the new parts still fit within a known volume envelope, the shape and location of the grooves can be chosen so that the sensors 116 and cameras 118 can be reconfigured for the new part 110 by moving them and securing them to new positions along the pre-existing grooves 122. The reconfiguration can be performed manually or by motors, servo-controllers or other mechanical advantage drivers including microelectromechanical (MEMS) devices, depending on the application and type of parts and detectors 114 that are used. The sensors 116 and other detectors 114 may be secured within their respective grooves 122 by locking devices (not shown). It may also be desirable to relocate some of the supports 122 along pre-existing apertures and slots on the substrate 124. For details regarding other relocatable supports and locking devices, reference is made to U.S. Pat. No. 5,943,750 to Koren et al., assigned to the assignee of the present invention.

In some applications, it may be desirable to use one inspection apparatus for two different families of parts, especially if the families of parts are closely related, by simply replacing a first set of supports constructed for a first family with a second set of supports constructed for a second family. Additionally, more than one inspection apparatuses may be placed on or along the production line and the same parts may be re-inspected at different stages of the manufacturing process, at different locations along the production line and at different orientations with respect to the inspection apparatuses.

The inspection apparatus may include vibration isolators 115, including shock absorbers, such as springs, dumpers, layers of vibration-absorbing materials, such as, for example, rubber, etc. The inspection apparatus may further include moving mechanical gages 172, i.e. gages that are attached to and move with the part 106. Additionally, one or more of the detectors 114, such as, for example, a camera 118, may be mounted on a support 121 that may either be held stationary or move so that that it follows the part 106 as it moves along the conveyor line 102.

The sensors 116 detect and measure one or more characteristics of the part 106. For an inspection apparatus 100 dedicated to cylinder heads, for example, the sensors 116 and cameras 118 are selected and configured to enable the inspection of parts with overall dimensions that are appropriate for the cylinder head part family. Other dimensions and configurations may be specified for different applications.

Examples of characteristics that may be measured within given tolerances, described in reference to, but not limited to the parts of FIGS. 2(a)–(b), include:

Parallelism, i.e. whether a first surface 136 is parallel to a second surface 138 within a given tolerance. The surfaces may be, for example, planar or curved. Parallelism may also be measured between edges.

Flatness of a surface, i.e. whether a surface or part of a surface, such as a first surface 136 or a second surface 138 is planar.

Surface roughness, i.e. the presence of surface irregularities, typically left on the part by the machining process.

Location of an aperture 140 relative to a given reference, such as, for example, edge 142, and diameter measurement.

Profile measurement of surfaces, such as profile 146 of surface 136 at a specified location.

Detection of a broken tool 144, such as a broken tap that is left in an aperture.

The above characteristics are representative of characteristics that may be detected and measured within given tolerances and accuracy. Other or additional characteristics with various accuracy and tolerance requirements may be selected for inspection and measurement depending on the application.

In one embodiment, the inspection apparatus may include a radio frequency (RF) identification system that incorporates one or more radio frequency readers, which preferably includes a transceiver (transmitter/receiver) unit. An entrance reader 126 is placed at the entrance 128, where the part 106 enters the inspection apparatus 100 so that it can read a radio frequency tag 130 attached on the fixture 112 or the part 106. The tag 130 is, preferably, a read/write tag. As the part 106 enters the inspection apparatus 100, the entrance reader 126 reads the part identification or other information written on the tag 130. As the part 106 exits the inspection apparatus 100 at exit 134, an exit reader 132 writes other information, such as the inspection outputs from the detectors 114, on the tag 130, as is explained herein below.

The inspection apparatus 100 may also include a computer system 148 that communicates with the detectors 114, including the sensors 116 and the cameras 118. The computer system 148 receives inspection outputs from the sensors 116 and images from the cameras 118 and analyzes them to present information accessible to an operator. The information may be presented on a screen display 150 in graphical or tabular form and may include comparisons with a stored design for the part, in the form of a computer-aided design (CAD) model for example, that serves as a template. Deviations from predetermined tolerances for selected characteristics of the part may be computed and presented. A keyboard or operator console 152 or other operator-controlled data input device allows an operator to select the presentation format and send the results to a printer or to other manufacturing equipment or to another computer station. The operator console 152 need not be located in physical proximity to the inspection machine. Remote connections, via the Internet, satellite or cellular communication technologies, enable the operator to control the inspection process from a distance. The operating system for computer system 148 may be any operating system, such as UNIX, DOS, WINDOWS, etc, which is compatible with the non-contact sensors and other original manufacturer equipment (OEM). Other computer architectures that may be used with the invention include a stand-alone computer, a computer communicating with an operator only, a computer communicating with another machine, a computer communicating with the production line, etc.

The computer system 148 may also interface with the transceiver units of the entrance tag reader 126 to receive the identification of the part 106 which is written on the tag 130. The computer system 148 may also interface with the exit tag reader 132, which reads and writes information on the tag 130 as the part 106 exits. The information written on the part 106 at the exit 134 of the inspection apparatus 100 may include, for example, the inspection outputs from the sensors 116. In addition or instead of the radio frequency identification system, a bar code system may be used, including a bar code reader 174 communicating with the computer system 148 and reading a bar code tag 176 attached on the part 106 or on the fixture 112.

Figure 3:
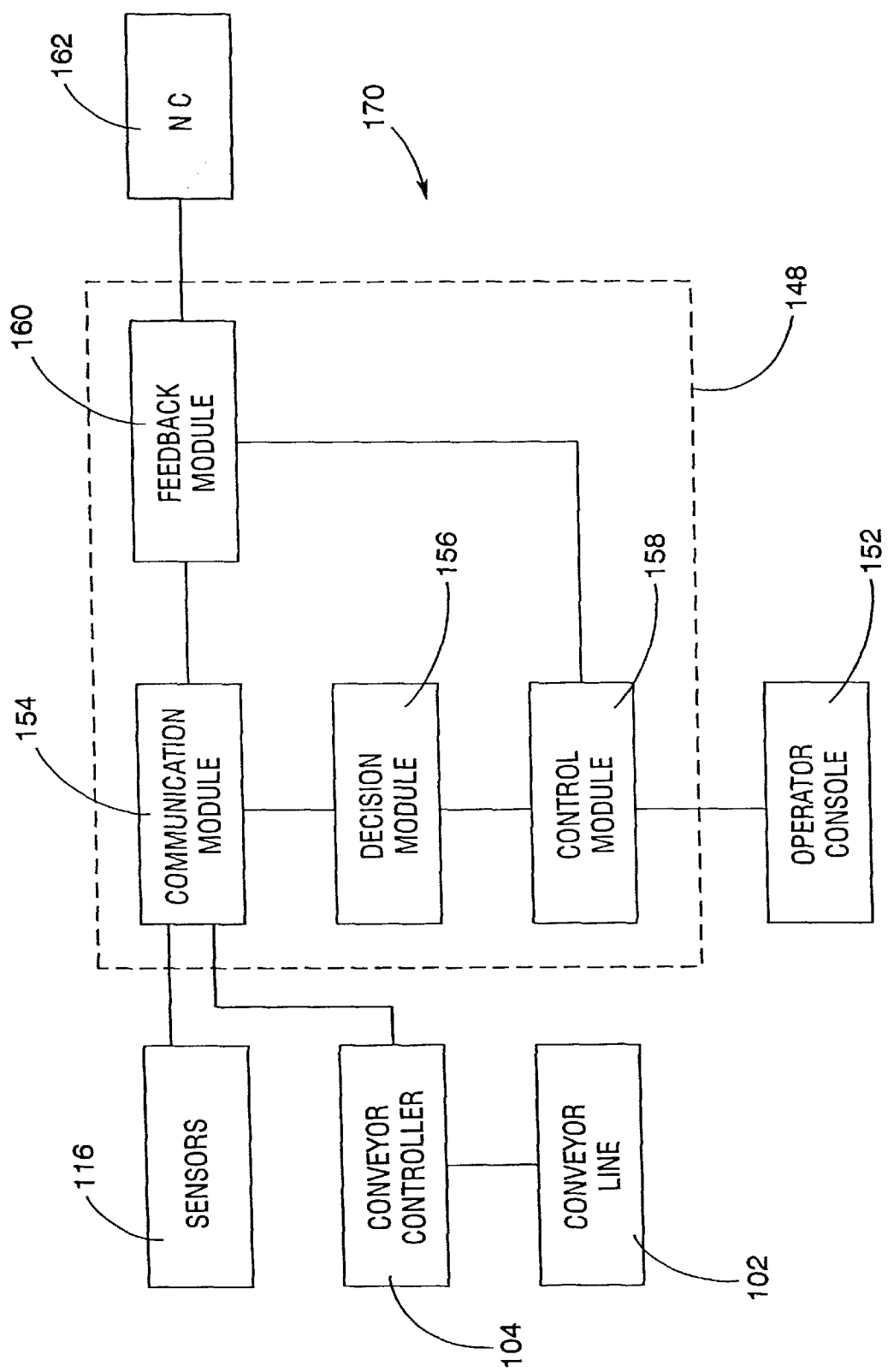
FIG. 3 is a diagrammatic view of an embodiment of an inspection system according to the invention.

As shown in an embodiment of an inspection system 170 in FIG. 3, the computer system 148 may include a communication module 154 for communicating with the sensors 116 and cameras 118, the conveyor controller 104 and other equipment as needed. A decision module 156 may be provided for analyzing the inspection outputs and images received from the sensors 116 and cameras 118, and a control module 158 may be provided as well. The control module 158 may issue, for example, a command to the conveyor controller 104 to stop the conveyor line 102 when a defect has being detected, or a command to discard a particular part. Other commands may be directed to the operator console 152 to provide warnings, request operator input, etc. The computer system 148 may also include a feedback module 160 that communicates with manufacturing or machining equipment, such as a numerical controller (NC) 162, to provide input to such equipment when defective parts or exceeded tolerances are detected. Based on input from the feedback module 160, the operation of the numerical controller 162 may be suspended or a particular predetermined path of the numerical controller 162 may be modified. Although the modules of the computer system 148 are herein described and shown in FIG. 3 as distinct for clarity, the modules may be integrated in one or more processors 164, as shown in FIG. 5.

The software for the modules of the computer system 148 and for interfacing the inspection apparatus 100 with other components such as, for example, the conveyor controller 104, or other equipment, such as, for example, the numerical controller 162, etc., is commercially available. Modifications or additions to such software are also within the purview of a person of ordinary skill in the art.

Figure 5:
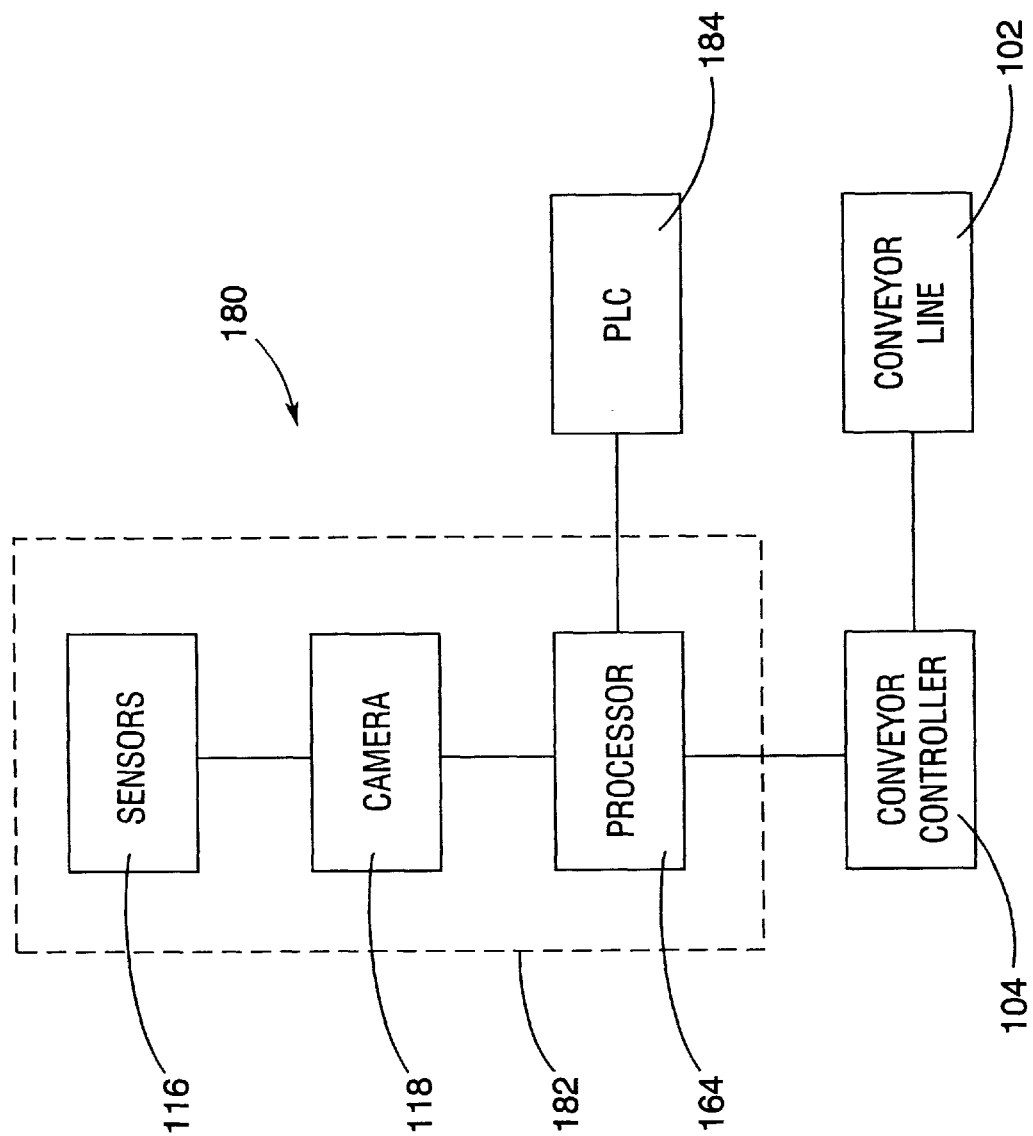
FIG. 5 is a diagrammatic view of another embodiment of an inspection system according to the invention.

Referring to FIG. 5, another embodiment of an inspection system 180, may include the sensors 116, cameras 118 and processor 164 to form an integrated machine vision system 182, which communicates with the conveyor controller 104 and a programmable logic controller (PLC) 184, which controls the operation of manufacturing/machining equipment for the parts 106.

When a new part 110 in the same family of parts is scheduled for production, the inspection apparatus 100 may quickly be reconfigured for the new part 110 by moving the sensors 116 and/or cameras 118 along their respective grooves 122 or relocating them to other grooves 122 for optimal detection of new profiles 166, new location of apertures 168, etc. Furthermore, some sensors 116 may be removed, or replaced with sensors of different type or specifications, or additional sensors may be added to the inspection apparatus 100, as needed. Alternatively, another inspection apparatus, identical in all respects, but reconfigured differently, may be used to re-inspect a part at a different stage of the manufacturing process or at a different orientation with respect to the inspection apparatuses.

Figure 4:
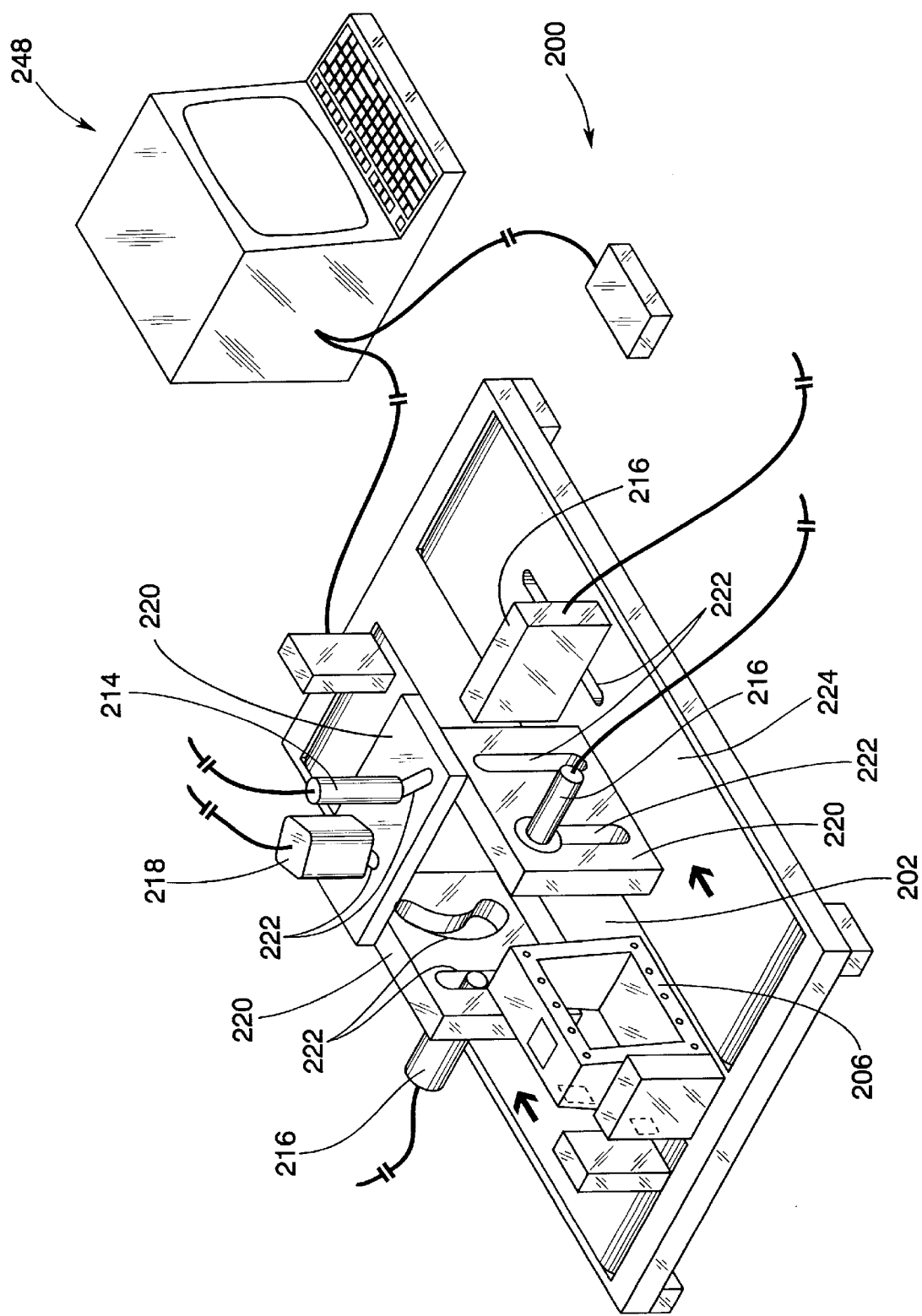
FIG. 4 is a schematic isometric view of another embodiment of an inspection apparatus according to the invention.

In an alternate embodiment of the inspection apparatus 200, shown in FIG. 4, the part 206 is placed on a stationary line 202 and the detectors 214, such as sensors 216, cameras 218, etc., are mounted on supports 220 that may move around the part 206. For example, the supports 220 may stand on moving lines 224, or the supports 220 may be robotic structures with independent motion, which may be controlled by a computer system 248. Regardless of the means of locomotion of the supports 220, any of the sensors 214 and cameras 218 may be reconfigurable in relation to the moving supports 220 using a plurality of grooves 222 on the supports, as explained herein above.

Figure 6:
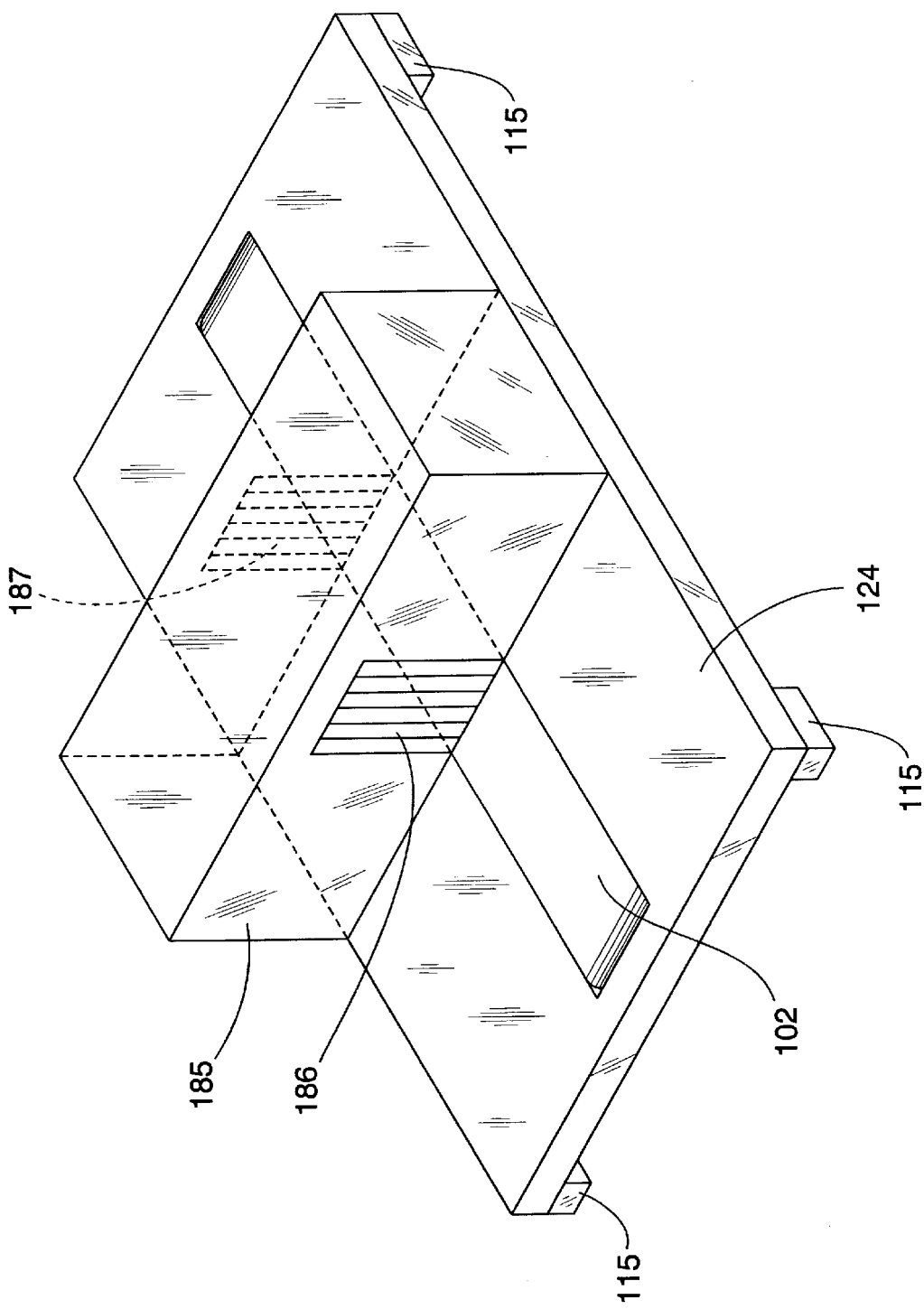
FIG. 6 is a schematic isometric view of an embodiment of an inspection apparatus with an environmentally-controlled chamber according to the invention.

The invention may also include an environmentally-controlled chamber 185 for enclosing one or more sensors, FIG. 6. The environmentally-controlled chamber 185 may provide, for example, temperature control, humidity control, differential pressure to prevent dust particles from entering the chamber 185, etc. The entrance door 186 and the exit door 187 to the chamber 185 allow passage of a part 106 with minimum disturbance to the protected environment inside the chamber 185, by the use of flexible strips, seals or other commercial protective closures. Additionally remote control identification devices for automatic opening the entrance and exit 185 as the part 106 approaches may also be used.

The invention also provides a method for part inspection during a manufacturing process. The method includes mounting a plurality of non-contact sensors 116 on stationary supports 120 in proximity to a moving line 102 holding a first part 106, measuring at least one characteristic of the first part, such as, for example, flatness, parallelism, etc., and producing an inspection output for the part 106, as discussed above. The method further includes converting the inspection output to operator-accessible information, which may be presented in graphical or tabular form on a display 150. The method further includes reconfiguring the sensors 116 when a second part, for example a new or redesigned part, which has at least one different characteristic, is to be inspected. Reconfiguring the sensors 116 includes moving the sensors along predetermined grooves 122 that have various shapes and sizes and are defined on the supports 120. The method may further include mounting a camera 118 on a stationary support 122 to scan or videotape the part 106 as it moves, or mounting a camera 218 on a moving support 220 to produce images of a part 206 that is stationary, or mounting the camera 118 on a moving support 121 that follows a moving part 106.

The invention also provides another method provides for inspecting and re-inspecting a part during a manufacturing process. The method includes mounting a plurality of non-contact sensors 116 on stationary supports 120 in proximity to a moving line 102 holding a part 106, measuring at least one characteristic of the part at a first stage of the manufacturing process and producing an inspection output for the part 106, as discussed above. The method further includes reconfiguring the sensors 116 for re-inspecting the part at a second stage of the manufacturing process.

Whereas particular embodiments of the invention have been described herein for the purpose of illustrating the invention and not for the purpose of limiting the same, it will be appreciated by those of ordinary skill in the art that numerous variations of the details, materials and arrangement of parts may be made within the principle and scope of the invention without departing from the invention as described in the appended claims.

What is claimed is:

1. An apparatus for inspecting a first part and a second part, the first and second parts belonging to a single family of parts, the apparatus comprising:

a conveyor line for moving the first part during a manufacturing process; and a plurality of non-contact sensors reconfigurably mounted in grooves on one or more stationary supports in proximity to the conveyor line, wherein the grooves have shape and location selected for the family of parts, the sensors being stationary relative to the supports during inspection, wherein at least one of the plurality of non-contact sensors measures at least one characteristic of the first part and produces an inspection output, the plurality of non-contact sensors being reconfigurable on the grooves for measuring at least one different characteristic of the second part.

2. The apparatus of claim 1, wherein the conveyor line is part of the production line.

3. The apparatus of claim 1, wherein the conveyor line is adjacent to the production line.

4. The apparatus of claim 1, further comprising a computer system that receives the inspection output and generates operator-accessible information about the first part.

5. The apparatus of claim 4, wherein the computer system controls the motion of the conveyor line from a remote location.

6. The apparatus of claim 1, further including stationary supports that are disposed along each side and above the conveyor line.

7. An apparatus for inspecting a part belonging to a family of parts, the apparatus comprising:

a conveyor line for moving the part during a manufacturing process; and a plurality of non-contact sensors reconfigurably mounted in grooves on one or more stationary supports in proximity to the conveyor line, wherein the grooves have shape and location selected for the family of parts, the sensors being stationary relative to the supports during inspection, wherein at least one of the plurality of non-contact sensors measures at least one characteristic of the part at a first stage of the manufacturing process and produces an inspection output, the plurality of non-contact sensors being reconfigurable on the grooves for re-inspecting the part at a second stage of the manufacturing process.

8. A system for inspecting a first part and a second part, wherein the first and second parts belong to a single family of parts, the system comprising:

a conveyor line for moving the first part during a manufacturing process;

a plurality of stationary supports disposed in proximity to the conveyor line, each support including a plurality of grooves, wherein the grooves have shape and location selected for the family of parts;

a plurality of electro-optical detectors reconfigurably mounted in any one of the grooves, wherein the detectors are stationary relative to the supports during inspection, each detector measuring a characteristic of the first part and producing an inspection output for the first part; and a computer system communicating with the detectors and converting the inspection outputs to operator-accessible information about the first part, and wherein the plurality of electro-optical detectors can be reconfigured on the grooves for inspection of at least one different characteristic of the second part.

9. The system of claim 8, wherein the conveyor line is part of the production line.

10. A system for inspecting a first part and a second part, the first and second parts belonging to a single family of parts, the system comprising:

a stationary line for holding the first part during a manufacturing process;

a plurality of supports moving in proximity and relative to the stationary line, each support including a plurality of grooves, wherein the grooves have shape and location selected for the family of parts;

a plurality of electro-optical detectors, wherein each detector is reconfigurably mounted in any one of the grooves to measure a characteristic of the first part and produce an inspection output for the first part, wherein each detector is stationary relative to its respective support during inspection; and a computer system communicating with the detectors and converting the inspection outputs to operator-accessible information about the first part, and wherein the detectors can be reconfigured on the grooves for inspection of at least one different characteristic of the second part.

11. A system for inspecting a first part and a second part, the first and second part belonging to a single family of parts, the system comprising:

at least one support moving in relation to the first part, the at least one support including a plurality of grooves, wherein the grooves have shape and location selected for the family of parts;

a plurality of electro-optical detectors, wherein each detector is reconfigurably mounted in anyone of the plurality of grooves to measure a characteristic of the first part and produce an inspection output for the first part, wherein each detector is stationary relative to its respective support during inspection; and a computer system communicating with the detectors and converting the inspection outputs to operator-accessible information about the first part, and wherein the detectors can be reconfigured on the grooves for inspection of at least one different characteristic of the second part.

12. A system for inspecting a first part and a second part, the first and second parts belonging to a single family of parts, the system comprising:

means for moving the first part during a manufacturing process;

detector means for measuring at least one characteristic of the first part and producing an inspection output for the first part;

processor means for converting the inspection output to operator-accessible information about the first part; and means for reconfiguring the detector means for inspection of at least one different characteristic of the second part, wherein the means for reconfiguring have shape and location selected for the family of parts and wherein the detector means are stationary relative to the means for reconfiguring during inspection.

13. A system for inspecting a part, the part belonging to a family of parts, the system comprising:

means for moving the part during a manufacturing process;

detector means for measuring at least one characteristic of the part during a first stage of the manufacturing process and producing an inspection output for the part;

processor means for converting the inspection output to operator-accessible information about the part; and means for reconfiguring the detector means for re-inspecting the part at a second stage of the manufacturing process, wherein the means for reconfiguring have shape and location selected for the family of parts and wherein the detector means are stationary relative to the means for reconfiguring during inspection.

14. A system for inspecting a first part and a second part, the first and second parts belonging to a single family of parts, the system comprising:
- a conveyor line connected to a conveyor controller for moving the first part during a manufacturing process;
- a plurality of stationary supports in proximity to the conveyor line;
- a plurality of non-contact sensors mounted on the stationary supports, wherein the sensors are reconfigurably mounted in grooves on the supports, the grooves having shape and location selected for the family of parts, wherein the sensors are stationary relative to the supports during inspection, and wherein each sensor measures at least one characteristic of the first part and produces an inspection output for the first part; and
- a computer system comprising:
  - a communication module in communication with the sensors and the conveyor controller;
  - a decision module that compares the inspection outputs for the first part with a computer-stored design of the first part within predetermined tolerances; and
  - a control module that issues a command when a tolerance is exceeded, and wherein the sensors can be reconfigured on the grooves for inspection of at least one different characteristic of the second part.

15. The system of claim 14, wherein the conveyor line is part of the production line.

16. The system of claim 14, wherein the conveyor line is adjacent to the production line.

17. A system for inspecting a first part and a second part, the first and second parts belonging to the same family of parts, the system comprising:
- a conveyor line for moving the first part during a manufacturing process;
- a plurality of stationary supports disposed in proximity to the conveyor line;
- a machine vision system comprising:
  - a plurality of non-contact sensors reconfigurably mounted in grooves on any one of the stationary supports, wherein the grooves have shape and location selected for the family of parts, the sensors being stationary relative to the supports during inspection, and the sensors measuring at least one characteristic of the first part and producing an inspection output for the first part;
  - at least one camera reconfigurably mounted in any one of the grooves on the stationary supports, the camera capturing an image of the first part; and
  - a machine vision processor in communication with the camera and the sensors to process the image and the inspection outputs and issue a command for the production of the first part, and wherein the sensors can be reconfigured on the grooves for inspection of at least one different characteristic of the second part.

18. The system of claim 17, wherein the machine vision command is sent to a programmable logic controller.

19. A method for inspecting a first part and a second part during a manufacturing process, the first and second parts belonging to a single family of parts, the method comprising:
- reconfigurably mounting a plurality of non-contact sensors in grooves on stationary supports in proximity to a moving line holding the first part, wherein the grooves have shape and location selected for the family of parts and wherein the sensors are stationary relative to the supports during inspection;
- measuring at least one characteristic of the first part and producing an inspection output for the first part;
- converting the inspection output to operator-accessible information; and
- reconfiguring the sensors on the grooves for inspection of at least one different characteristic of the second part.

20. The method of claim 19, wherein measuring includes detecting by non-contact sensors.

21. A method for inspecting a first part and a second part during a manufacturing process, the first and second part belonging to a single family of parts, the method comprising:
- reconfigurably mounting a plurality of non-contact electro-optical sensors in grooves on supports in proximity to a moving line holding the first part, wherein the grooves have shape and location selected for the family of parts and wherein the sensors are stationary relative to the supports during inspection;
- reconfigurably mounting at least one camera in any one of the grooves, the camera being in communication with the sensors and directed to the moving line;
- measuring at least one characteristic of the first part and producing an inspection output that includes an image of the first part;
- converting the inspection output to operator-accessible information; and
- reconfiguring the sensors and the camera on the grooves for inspection of at least one different characteristic of the second part.

22. The method of claim 21, wherein the camera is mounted on a moving support.

23. A method for inspecting and re-inspecting a part during a manufacturing process, wherein the part belongs to a family of parts, the method comprising:
- reconfigurably mounting a plurality of non-contact sensors in grooves on supports in proximity to a moving line holding the part, wherein the grooves have shape and location selected for the family of parts and wherein the sensors are stationary relative to the supports during inspection;
- measuring at least one characteristic of the part at a first stage of the manufacturing process and producing an inspection output for the part;
- converting the inspection output to operator-accessible information; and
- reconfiguring the sensors on the grooves for re-inspecting the part at a second stage of the manufacturing process.

* * * * *